US008992231B2

(12) United States Patent
Betrouni et al.

(10) Patent No.: US 8,992,231 B2
(45) Date of Patent: Mar. 31, 2015

(54) PROSTATE PHANTOM, SYSTEM FOR PLANNING A FOCAL THERAPY OF A PROSTATE CANCER COMPRISING SUCH PROSTATE PHANTOM AND METHOD FOR PLANNING A FOCAL THERAPY OF A PROSTATE CANCER IMPLEMENTING SUCH SYSTEM

(71) Applicants: Nacim Betrouni, Loos (FR); Bertrand Leroux, Loos (FR); Pierre Colin, Lille (FR); Pierre Nevoux, Pointe-a-Pitre Cedex (FR); Serge Mordon, Loos (FR)

(72) Inventors: Nacim Betrouni, Loos (FR); Bertrand Leroux, Loos (FR); Pierre Colin, Lille (FR); Pierre Nevoux, Pointe-a-Pitre Cedex (FR); Serge Mordon, Loos (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 0 days.

(21) Appl. No.: 14/359,747

(22) PCT Filed: Nov. 20, 2012

(86) PCT No.: PCT/EP2012/073063
§ 371 (c)(1),
(2) Date: May 21, 2014

(87) PCT Pub. No.: WO2013/076056
PCT Pub. Date: May 30, 2013

(65) Prior Publication Data
US 2014/0306126 A1     Oct. 16, 2014

(30) Foreign Application Priority Data

Nov. 21, 2011   (EP) .................................. 11306523

(51) Int. Cl.
*G09B 23/32*     (2006.01)
*A61N 5/10*      (2006.01)
(Continued)

(52) U.S. Cl.
CPC ................ *A61N 5/103* (2013.01); *G09B 23/30* (2013.01); *G09B 23/32* (2013.01); *G01N 27/72* (2013.01); *G01N 29/30* (2013.01)
USPC ........................... 434/262; 434/267; 434/272

(58) Field of Classification Search
USPC .......................................... 434/262, 267, 272
See application file for complete search history.

(56) References Cited

U.S. PATENT DOCUMENTS 7,544,062 B1    6/2009  Hauschild et al.
2008/0076099 A1*  3/2008  Sarvazyan et al. ............ 434/262
(Continued)

FOREIGN PATENT DOCUMENTS

GB        2305289 A      4/1997
WO       00/13591       3/2000
(Continued)

*Primary Examiner* — Kiet T Nguyen
(74) *Attorney, Agent, or Firm* — Whitham Curtis Christofferson & Cook, PC

(57) ABSTRACT

Prostate phantom comprising an artificial prostate (1) and an artificial lesion arranged within the artificial prostate (1), wherein the artificial prostate (1) comprises: a first part (1a) mimicking a peripheral zone of a zonal anatomy of the prostate, the first part (1a) being made of a first artificial tissue and comprising a closed outer surface, at least a second part (1b) separate from the first part (1a) and mimicking at least a second zone of the zonal anatomy of the prostate, the second part (1b) being made of a second artificial tissue and comprising a closed outer surface, the first (1a) and second (1b) parts contacting each other along an interface mimicking a boundary between the peripheral zone and the second zone.

15 Claims, 5 Drawing Sheets

Figure 1:
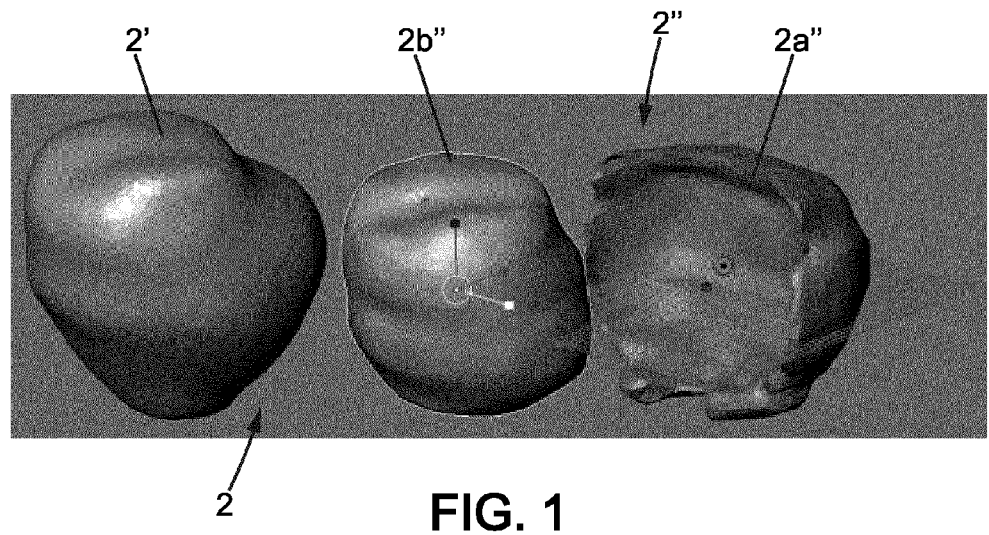

(51) Int. Cl.
*G09B 23/30* (2006.01)
*G01N 27/72* (2006.01)
*G01N 29/30* (2006.01)

(56) References Cited

U.S. PATENT DOCUMENTS

2010/0198063 A1* 8/2010 Huber et al. .................. 600/437
2014/0073907 A1* 3/2014 Kumar et al. ................. 600/414

FOREIGN PATENT DOCUMENTS

| WO | 2008/021720 A2 | 2/2008 |
| WO | 2008/024397 A2 | 2/2008 |

* cited by examiner

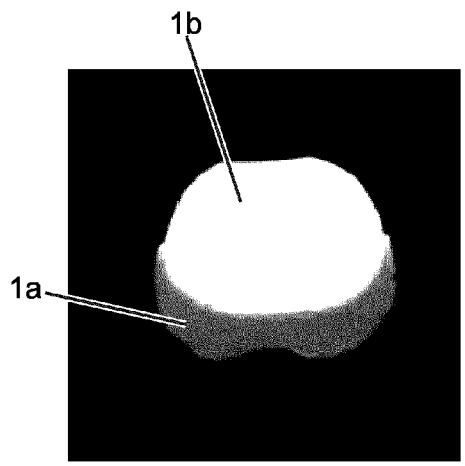
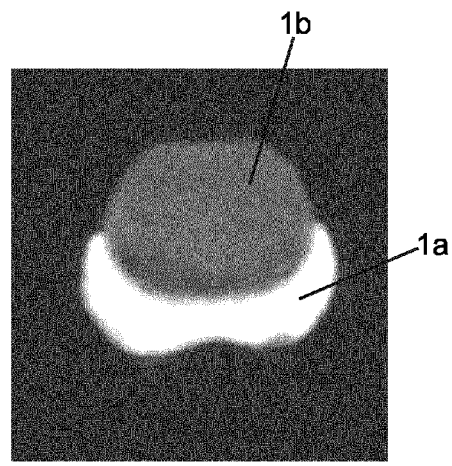
FIG. 6a          FIG. 6b
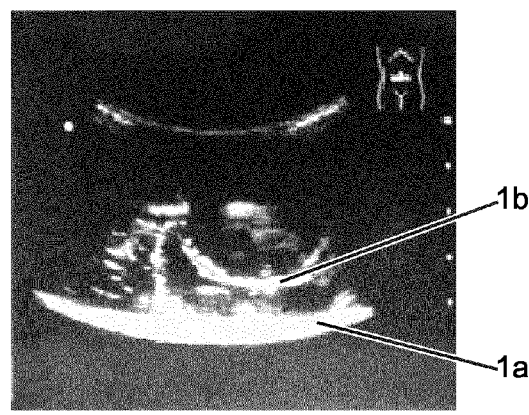
FIG. 6c

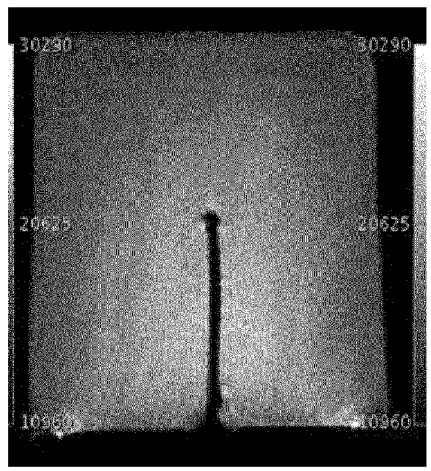 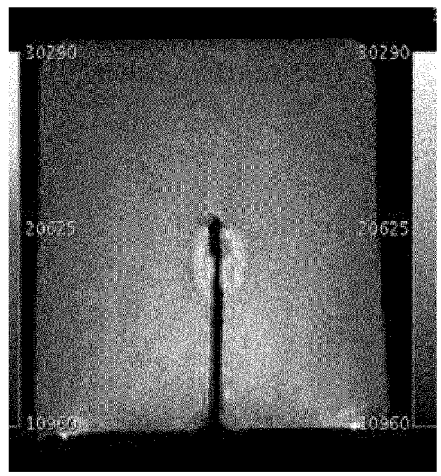
FIG. 7a  FIG. 7b
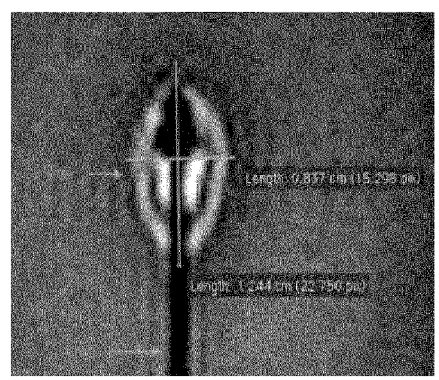
FIG. 8a
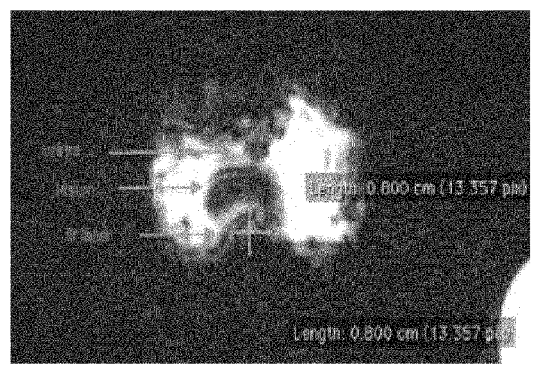
FIG. 8b

PROSTATE PHANTOM, SYSTEM FOR PLANNING A FOCAL THERAPY OF A PROSTATE CANCER COMPRISING SUCH PROSTATE PHANTOM AND METHOD FOR PLANNING A FOCAL THERAPY OF A PROSTATE CANCER IMPLEMENTING SUCH SYSTEM

The invention relates to a prostate phantom, to a system for planning a focal therapy of a prostate cancer comprising such prostate phantom and to a method for planning a focal therapy of a prostate cancer implementing such system.

From a morphologic point of view, the prostate is an exocrine gland, shaped like a pyramid with an upward base. A zonal anatomy of the prostate has been described for the first time in the 60's, but the use of terms in anatomical practice was introduced in the 80's. According to the zonal anatomy, the prostate is composed of four zones: a peripheral zone (PZ), a central zone, a transition zone (TZ) and a fibromuscular structure. The peripheral zone and the transitional zone are key structures, as 70% of prostate tumours are located within the peripheral zone. Inversely, benign hypertrophy (BPH) most often occurs in the transition zone, which becomes larger with age.

Prostate cancer remains the most commonly occurring malignancy among men in the developed countries. For its support, many researches are undertaken in different aspects including diagnosis, prognostication and treatment. Thereby, many procedures were developed to assist the clinician. For instance, the diagnosis has experienced an important development through the combination of prostatic specific antigen (PSA), digital rectal examination (DRE) and image-guided biopsy by transrectal ultrasound (TRUS) or magnetic resonance imaging (MRI). For the treatment, in addition to conventional techniques, such as prostatectomy, radiotherapy and brachytherapy, a concept of focal therapies is emerging where the aim is to treat only the tumour. These focal therapies constitute an intermediate option between watchful waiting and radical therapy for small volume and low-grade prostate cancer.

Validation and optimization of new therapies, such as focal therapies, in the treatment of prostate cancer require the use of prostate phantoms for simulation. Besides in these new therapies, imaging takes an increasingly growing position and image analysis has become crucial to control the therapy and to validate its efficiency.

Phantoms for planning a therapy of a prostate cancer are known. Such known prostate phantom, disclosed for example in document WO 2008/021720, generally comprises an artificial prostate having an outer surface shaped to conform to a real prostate, and an artificial lesion arranged within the artificial prostate. The artificial prostate is made to provide a contrast different from that of the artificial lesion on an image acquired according to a first imaging modality, and the artificial lesion is made to provide a contrast different from that of the artificial prostate on an image acquired according to a second imaging modality, the second imaging modality being different from the first imaging modality. Document WO 2008/021720 also discloses artificial peripheral tissues surrounding the artificial prostate and therefore arranged outside its outer surface.

There remains, however, a need of a prostate phantom that is anatomically valid and that matches closely the anatomical structure of the prostate.

The invention aims to meet the above mentioned need.

To this end, according to a first aspect, the invention proposes a prostate phantom for planning a focal therapy of a prostate cancer, said prostate phantom comprising an artificial prostate having an outer surface shaped to conform to a real prostate, and an artificial lesion arranged within the artificial prostate, said artificial prostate providing for a contrast different from that of the artificial lesion on an image acquired according to a first imaging modality, and said artificial lesion providing for a contrast different from that of the artificial prostate on an image acquired according to a second imaging modality, said second imaging modality being different from the first imaging modality, wherein the artificial prostate comprises:
  a first part mimicking a peripheral zone of a zonal anatomy of the prostate, the first part being made of a first artificial tissue and comprising a closed outer surface,
  at least a second part separate from the first part and mimicking at least a second zone of the zonal anatomy of the prostate, the second part being made of a second artificial tissue and comprising a closed outer surface,
  the first and second parts contacting each other along an interface mimicking a boundary between the peripheral zone and the second zone.

Hence, the artificial prostate of the invention which is composed of different parts arranged within its outer surface and which mimics the anatomical structure of the prostate is anatomically valid. The interface between the first and second parts can be detected on images acquired by the first and second imaging modalities so as to accurately distinguish the two parts.

According to some provisions, the first and second parts and the artificial lesion can easily be modulated in size and relative arrangement to offer a wide range of different experimentations, for example depending on the location of the artificial lesion.

According to some provisions, the artificial prostate of the invention may have optical properties close to that of the human prostate and allow visualization by both magnetic resonance imaging and ultrasound imaging.

According to some provisions, the prostate phantom of the invention allows transrectal and trans-perineal access.

According to some provisions, the different parts of the prostate phantom are thermally responsive making it possible to target lesions by thermotherapy procedure using an interstitial laser.

In particular, in some embodiments, the phantom prostate of the invention may have one or several of the following provisions:
  the first artificial tissue and the second artificial tissue are different from each other to provide respective different contrasts on an image acquired according to the first imaging modality and on an image acquired according to the second imaging modality,
  each of the first and second artificial tissues comprises:
  a ballistic gel made of gelatine between 1% w/w and 10% w/w, preferably 4% w/w, and water between 90% w/w and 99% w/w, preferably 96% w/w,
  a first contrast agent visible on the image acquired according to the first imaging modality, a concentration of the first contrast agent for the first artificial tissue being different from a concentration of the first contrast agent for the second artificial tissue,
  the first contrast agent comprises gadolinium visible on the image acquired by magnetic resonance imaging,
  the first part is moulded over the second part,
  the artificial lesion is made of a third artificial tissue comprising:

a ballistic gel made of gelatine between 1% w/w and 10% w/w, preferably 4% w/w, and water between 90% w/w and 99% w/w, preferably 96% w/w,
a second contrast agent visible on the image acquired according to the second imaging modality
the second contrast agent comprises haemoglobin visible on the image acquired by ultrasound sonography,
the artificial lesion is placed within the first artificial tissue,
the outer surface of the artificial prostate defines an internal volume between 30 cc and 80 cc, preferably between 40 cc and 50 cc,
the prostate phantom further comprises an external mould having an outer surface and including internally a cavity for accommodating the artificial prostate, the external mould comprising:
a first conduit having a wall arranged close to the cavity, and an end opening in the outer surface, said first conduit mimicking a rectum with an anal orifice,
a second conduit having a wall and two ends opening in the outer surface and in the cavity, respectively, said second conduit mimicking an urethra,
at least the walls of the first and second conduits being made of a material mimicking a perineal tissue.

According to a second aspect, the invention proposes a system for planning a focal therapy of a prostate cancer, said system comprising:
a prostate phantom as defined above,
an interstitial thermotherapy laser comprising a laser source for emitting a light energy and at least one optical fibre connected to the laser source for guiding the light energy,
a first imaging device for acquiring an image of the prostate phantom according to a first imaging modality,
a second imaging device for acquiring an image of the prostate phantom according to a second imaging modality.

The first imaging device may be a magnetic resonance imaging device.

The second imaging device may be an ultrasound sonography device.

According to a third aspect, the invention proposes a method for planning a focal therapy of a prostate cancer implementing a system as defined above, said method comprising the step of treating the artificial lesion by placing the optical fibre within the prostate phantom and emitting the light energy by the laser source while imaging the prostate phantom with at least one of the first and second imaging devices.

The method may comprise a step of accommodating the artificial prostate in a cavity internally formed in an external mould having an outer surface, the external mould comprising:
a first conduit having a wall arranged close to the cavity, and an end opening in the outer surface, said first conduit mimicking a rectum with an anal orifice,
a second conduit having a wall and two ends opening in the outer surface and in the cavity, respectively, said second conduit mimicking an urethra,
at least the walls of the first and second conduits being made of a material mimicking a perineal tissue,
wherein the step of treating the artificial lesion may comprise imaging the prostate phantom by magnetic resonance imaging and transrectal ultrasound sonography.

Figure 2:
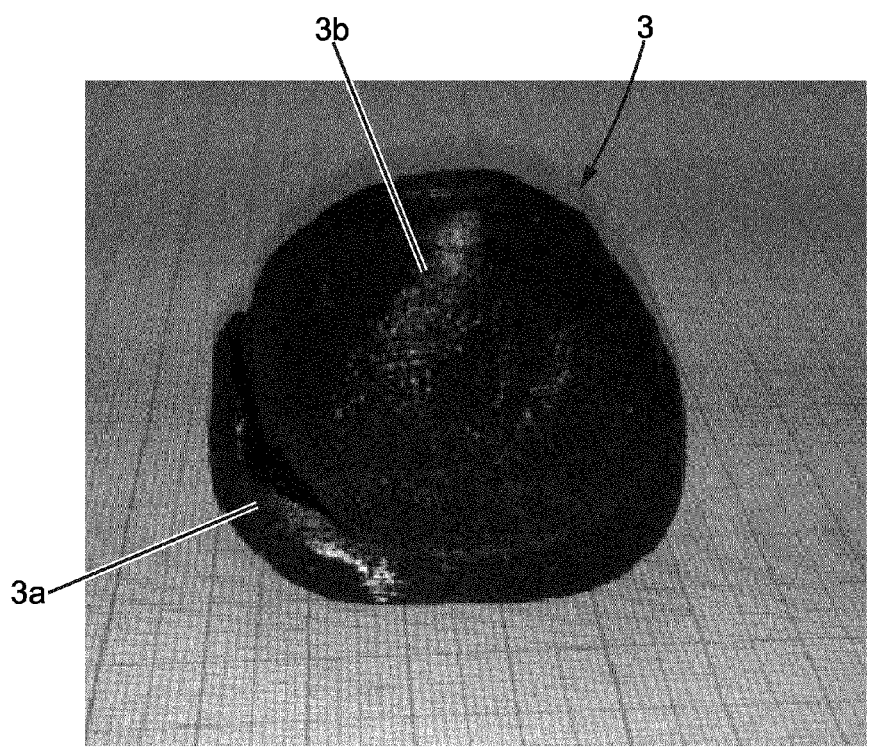
Figure 3A:
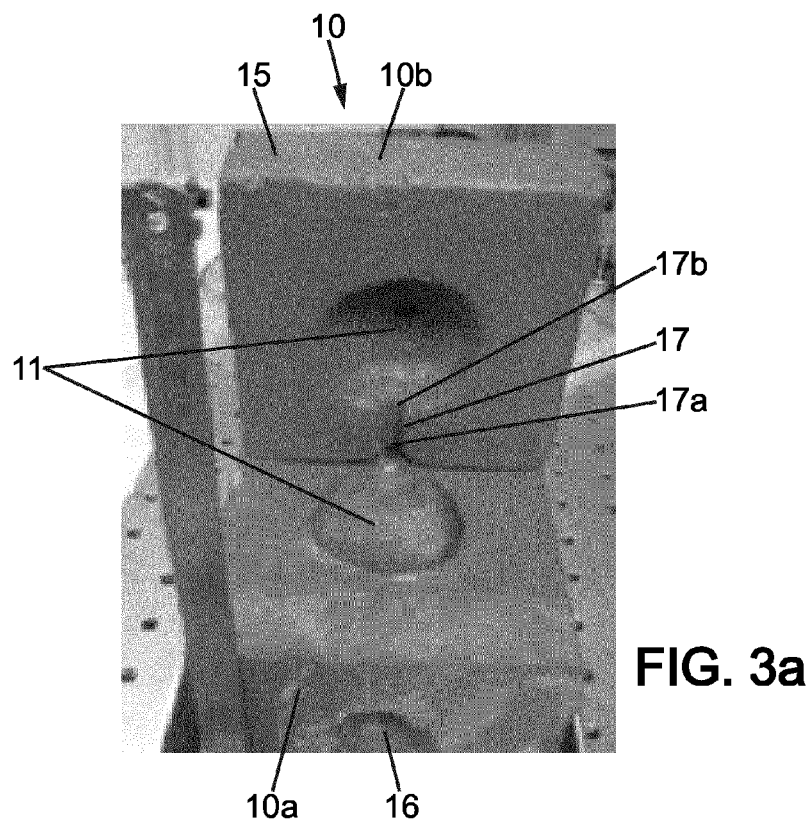
Figure 3B:
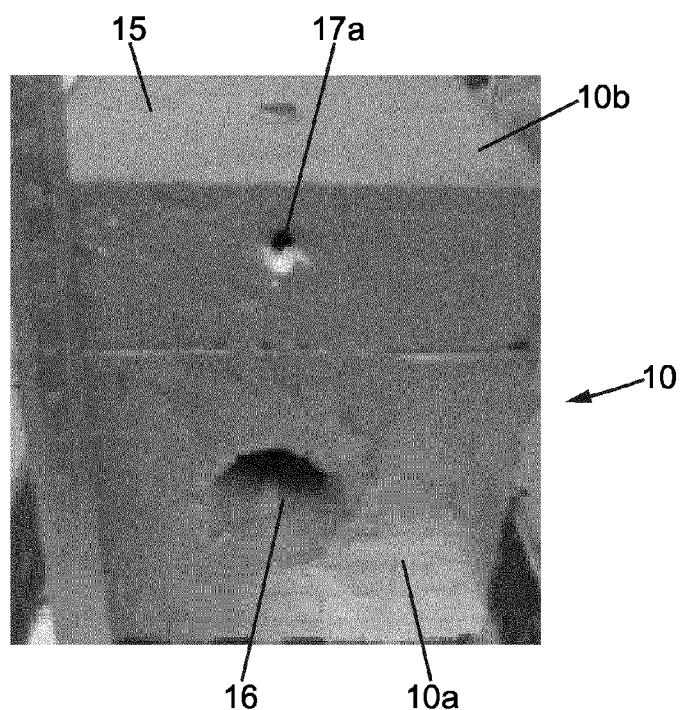
Figure 4:
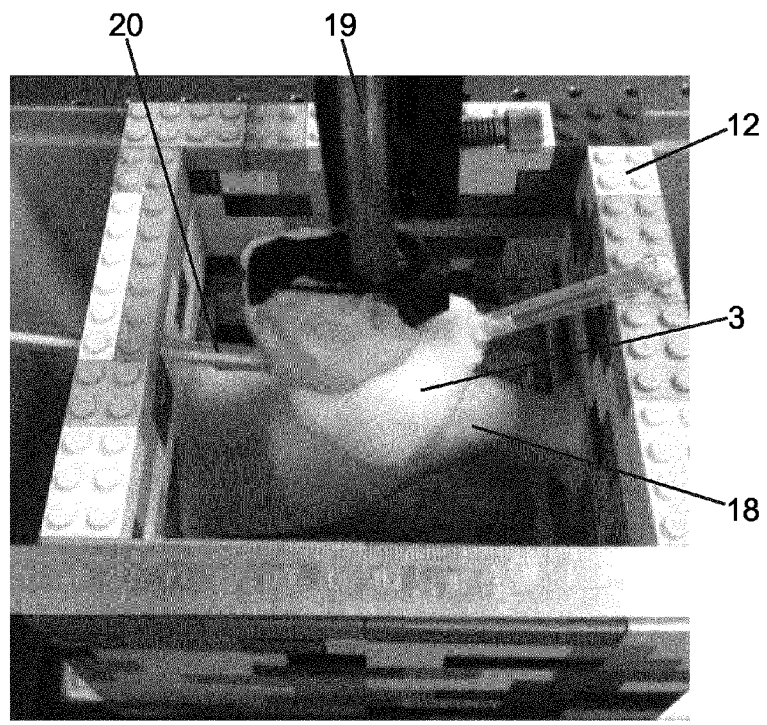
Figure 5:
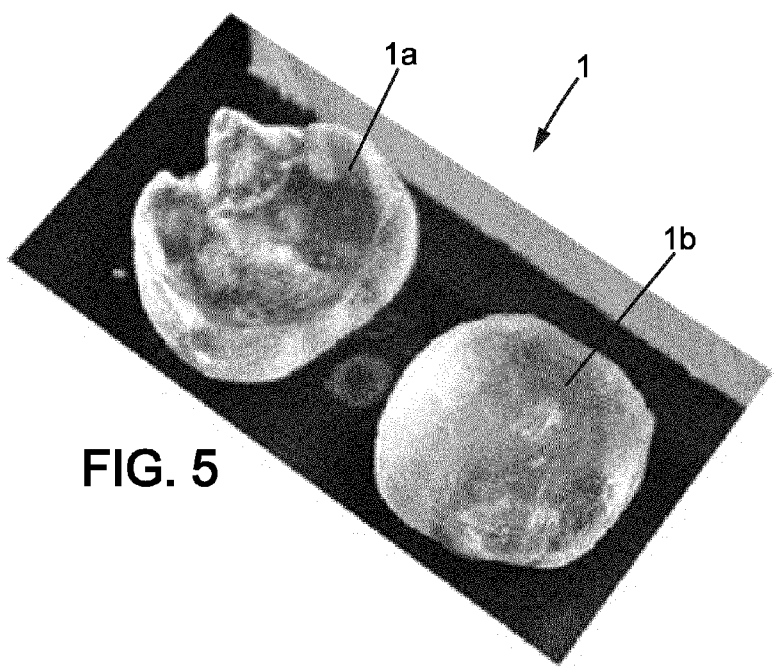

Other objects and advantages of the invention will emerge from the following disclosure of particular embodiments of the invention given as non limitative example, the disclosure being made in reference to the enclosed drawings in which:

FIG. 1 is a view of a prostate digital model used in a manufacturing method of a prostate phantom according to an embodiment of the invention, the prostate digital model comprising a gland digital model in which the whole prostate is in one part, and a transition and peripheral zone digital model in which the prostate is in two parts corresponding to a transition zone and a peripheral zone of the zonal anatomy of the prostate, FIG. 2 is a view of a prostate solid 3D model in two parts obtained from the transition and peripheral zone digital model of the prostate digital model of FIG. 1 by 3D printing in the manufacturing method of the prostate phantom, FIGS. 3a and 3b are views of an external mould of the prostate phantom mimicking the main parts of a human body surrounding a prostate, the external mould being shown respectively in an opened state to access a cavity for an artificial prostate, and a closed state, FIG. 4 is a view of a casing housing the prostate solid 3D model of FIG. 2 for moulding the external mould of FIGS. 3a and 3b in the manufacturing method of the prostate phantom, FIG. 5 is a view of the artificial prostate made of two artificial tissues mimicking the transition and the peripheral zones, FIGS. 6a, 6b and 6c are respectively T2 weighted magnetic resonance image, proton density weighted magnetic resonance image and B-mode ultrasound image of the artificial prostate, FIG. 7 are MR images of thermal effect of a laser of a focal therapy on the artificial tissues, illustrating (a) a trajectory of an optical fiber of a system for planning a focal therapy and (b) thermal effect around a tip of the fiber, FIGS. 8a and 8b are MR images of the thermal effect of the laser on the phantom.

On the Figures, the same reference numbers refer to the same or similar elements.

In relation to the drawings, a prostate phantom mimicking a real prostate having a cancer and the main parts of a human body surrounding the prostate is disclosed. To that end, the prostate phantom comprises an external mould 10, an artificial prostate 1 arranged within the external mould 10 and an artificial lesion arranged within the artificial prostate 1.

As it will become apparent from the following description of the invention, the artificial prostate 1 has an outer surface shaped to conform to a real prostate, and comprises several parts separated from each other by interfaces. The different parts of the artificial prostate 1 correspond to different defined zones separated from each other by boundaries of a zonal anatomy of the prostate. In particular, the different parts may correspond to a peripheral zone, a central zone, a transition zone and a fibro-muscular structure of the zonal anatomy of the prostate.

In the disclosed embodiment, the artificial prostate 1 comprises first 1a and second 1b parts corresponding respectively to the peripheral zone and to the transition zone. Actually, such model is valid from a radiologic point of view for men aged over 50 years whose prostate is mainly composed of these two zones. Of course, the invention is not limited to this embodiment and other zones could be considered with corresponding parts in the artificial prostate 1.

The features of the prostate phantom will now be described in relation to a manufacturing method of the prostate phantom.

Generally speaking, the manufacturing process comprises:
creation of a digital model 2 by a computer,
3D printing of a solid 3D model 3 by a rapid prototyping station, moulding of the external mould 10 with a cavity 11 adapted to accommodate to the artificial prostate 1 by a casing 12 housing the solid 3D model 3, moulding of the artificial prostate 1 and the artificial lesion within the cavity 11 of the external mould 10.

Specific embodiments of the above mentioned steps of the manufacturing method of the prostate phantom will now be described as an illustrative example. The manufacturing steps are not limited to the embodiments disclosed and could be otherwise performed.

For the creation of the digital model 2, an image data base containing images from 30 patients suspected with prostate cancer was collected.

To selection of the patients was based on the following considerations.

The median age of prostate cancer diagnosis is 74 years, with nearly 66% of cases diagnosed after the age of 70. Before 50 the percentage is about 0.3%. Exams consist of prostate specific antigen (PSA) measurements coupled with rectal examination for men from 50 to 75. The normal volume of a young man prostate is 20-30 cc. It was found that 50% of men have prostate benign hypertrophy before 60, this percentage increases to 90% for men of 85. In a longitudinal study conducted on 1688 men aged from 50-75, it was shown that the sole factor influencing the prostate size was the age.

Images were segmented to extract the prostatic gland, the peripheral and the transition zones. The individual structures were analyzed using statistical shape analysis based on the Principal Component Analysis method to extract a morphologic description: mean shape and deviations. The complete procedure for this segmentation is described in Article "ProstAtlas: A digital morphologic atlas of the prostate", Betrouni et al., European Journal of Radiology, 2011.

As can be seen on FIG. 1, this modeling allows describing the prostate as a unique gland in a gland digital model 2' or to model it as two separate zones in a transition and peripheral zone digital model 2" comprising a peripheral zone digital model 2a" and a transition zone digital model 2b", to target more precisely a region. It allows also creating prostate with different volumes and morphologies by varying the deviation around the mean shape and thus be close to the real clinical data.

A 3D prostatic surface was computed and smoothed with the software Blender™. Prostate data thus obtained were exported on Matlab™ to obtain a model of the desired volume with the desired dimensions. The file obtained in blend ou 3ds format was exported to a STL (for stereolithography) file in the software Blender™ for use by the software of the rapid prototyping station. The rapid prototyping station was the 3D printer designjet-3d-hp® and the material used to make the solid 3D model of the prostate was thermoformable plastic ABS-M30®.

Using 3D-printing, a prostate solid 3D model 3 in two parts, shown on FIG. 2, can be obtained from the transition and peripheral zone digital model 2" of the prostate digital model 2. The prostate solid 3D model 3 comprises two separate parts, namely a peripheral zone solid model 3a and a transition zone solid model 3b having shapes corresponding respectively to that of the peripheral zone and to the transition zone.

External Mould 10

The external mould 10 mimics the perineum, the rectum, the prostate cavity and the urethra.

As shown on FIGS. 3a and 3b, the external mould 10 has an outer surface 15 and includes internally a cavity 11 for accommodating the artificial prostate 1. The external mould 10 is parallelepipedic and made of two distinct parts: a lower base 10a and a removable upper part 10b, the cavity 11 being formed at the interface of these two parts. The removable upper part 10b makes it possible to access the artificial prostate 1 for a macroscopic study and for replacement after treatment. The external mould 10 comprises different anatomical elements:

in the lower base 10a: a first conduit having a wall arranged close to the cavity 11, and an end opening 16 in the outer surface 15, said first conduit mimicking a rectum with an anal orifice, allowing introduction of an ultrasonic probe by endorectal route, in the upper part 10b: a second conduit 17 having a wall and two ends 17a, 17b opening in the outer surface 15 and in the cavity 11, respectively, said second conduit 17 mimicking an urethra.

The walls of the first and second 17 conduits are made of a material mimicking a perineal tissue.

In the lower base 10a and in the upper part 10b, introduction of thermocouples makes it possible to mimic nervous vascular bands and musculus urethral sphincter.

The arrangement of the different anatomical elements in the external mould 10 is made according to anatomical ratios. The configuration of the external mould 10 corresponds to a small pelvis of a human in supine position, equivalent to the position during a treatment by focal therapy, during biopsies or during prostatic imaging (MRI or ultrasound sonography). The distance between the prostatic apex and the anal orifice is between 30 mm and 40 mm, the distance between the rectal lumen and the posterior face of the prostate is less than 5 mm, the distance between the prostatic apex and the musculus sphincter is between 3 mm and 13 mm, vascular nervous bands are in contact with the lateral basal part of the prostate and at 2 mm from the Levator Ani at its apical part.

As shown on FIG. 4, the external mould 10 was constructed in the following way:

formation of a 10 cm-square casing 12 made of plastic construction bricks cube (Lego®), setup and fixation of the rectum 18 to a wall of the casing 12 with plasticine (flexible Plastiline® 1150T-x1), setup and fixation of the solid 3D model 3 of the prostate inside the casing 12 at a distance of 5 mm from the rectum 18 using a fixed lever arm 19, implementation of a urethral catheter 20 and sealing using plasticine to form urethra, preparation of the material for the external mould 10: addition of a catalyst to a silicone (silicone RTV 139 Esprit Composite®), coating of each part installed within the casing 12 with a thin layer of Vaseline, pouring of the material up to half of the solid 3D model 3 of the prostate, to form the lower base 10a of the external mould 10, solidification of the material: 24 hours of rest, addition of a thin layer of Vaseline on the lower base 10a and withdrawal of the lever arm 19 holding the solid 3D model 3 of the prostate in position, pouring of the material on the lower base 10a to form the upper part 10b of the external mould 10, solidification of the material: 24 hours of rest, moulding off of the external mould 10 from the casing 12.

Artificial Prostate

Gland Model

A gland model of the artificial prostate is made of a ballistic gel made of gelatine between 1% w/w and 10% w/w, preferably 4% w/w, and water between 90% w/w and 99% w/w, preferably 96% w/w.

The ballistic gel is, for example, porcine gelatine (300 Bloom, Sigma-Aldrich), a variation of Ordnance gelatine for ballistic studies (Fackler & Malinowski, Am J Forensic Med Pathol, Vol, 9, N° 3, 1988). Porcine gelatine is put into solution by heating it in purified water at 40° C. The solution can be maintained in that fused state indefinitely until it is cooled. It then congeals and forms the gel searched for. That gel can be fused back into liquid if exposed to 40° C. or more. It has been demonstrated that, though it still congeals at ambient temperature, its effectiveness as a reticulate gel is lessened if the temperature set for fusion is too high (much softer at 70° C., for example).

The usual volume of preparation is approximately 80 mL, for a concentration of 4% (weight/volume).

The ballistic gel has been modified by introducing a first contrast agent visible on the image acquired according to a first imaging modality. In particular, the first contrast agent gadolinium (Gadovist from Bayer, Dotarem from Guerbet), visible on the image acquired by magnetic resonance imaging (MRI), as first imaging modality. The gadolinium was introduced in a concentration of $6\ 25 \cdot 10^{-3}$ mmol·mL$^{-1}$, while the gel was still fused.

Gadolinium is visible to MRI and then usually used (intravascular) for the contrast it provokes between organic tissues, according to their level of vascularisation. It is used here at that concentration because it makes the gelatine-made model all the more observable by MRI during a calorific laser exposure.

Transition and Peripheral Zones Models

As indicated above, according to a preferred embodiment, the artificial prostate 1 comprises a first part 1a made of a first artificial tissue and mimicking the peripheral zone of the prostate, and a second part 1b made of a second artificial tissue and mimicking the transition zone of the prostate.

The first artificial tissue and the second artificial tissue can be different from each other to provide respective different contrasts on an image acquired according to the first imaging modality and on an image acquired according to a second imaging modality, such as ultrasound sonography.

In the implemented embodiment, the first and second artificial tissues are made using the same procedure as for the above disclosed gland model and by varying the gadolinium concentrations in order to obtain modular elements and identified structures on magnetic resonance and ultrasound images, as first and second imaging modalities.

The following concentrations were used:
0.00825 mmol·mL$^{-1}$ for the first artificial tissue of the peripheral zone,
0.00425 mmol·mL$^{-1}$ for the second artificial tissue of the transition zone.

Artificial Lesion

The artificial lesion is made of a third artificial tissue comprising:
  a ballistic gel made of gelatine between 1% w/w and 10% w/w, preferably 4% w/w, and water between 90% w/w and 99% w/w, preferably 96% w/w,
  a second contrast agent visible on the image acquired according to the second imaging modality.

The second contrast agent comprises haemoglobin visible on the image acquired by ultrasound sonography.

The base compound was lyophilized porcine haemoglobin (Sigma-Aldrich). It was used to prepare a suspension at 20 mg·mL$^{-1}$ in purified water. That suspension was then mixed with the fused gel at 40° C. (20% volume/volume) and the solution was homogenised.

The iron in the haemoglobin gives that gel a different appearance in MRI, and a different reactivity to laser shots.

These differences make that gel a perfect one for creating an internal zone in the main gel, simulating a tumour mass as artificial lesion, in the artificial prostate.

The haemoglobin-added gel is prepared and cooled at 4° C. It is then carved to obtain the approximated volume and shape of a credible prostate tumour mass.

Optionally, a target for example in the form of a millimetric ball such as a radiology marker X-Spot meditest®, Sigma can be added to the gel.

The peripheral zone solid model 3a of the solid 3D model 3 is arranged in the cavity 11 and the second artificial tissue is poured into the cavity 11 of the external mould 10 to form the second part 1b corresponding to the transition zone over peripheral zone solid model 3a. After the second artificial tissue has sufficiently cooled, the tumour mass is then inserted in the cavity 11 of the external mould 10 and the peripheral zone solid model 3a is removed from the cavity 11. The first artificial tissue is then poured into the cavity 11 over the tumour mass and the second artificial tissue to form the first part 1a corresponding to the peripheral zone. In the described embodiment, the first part 1a is moulded over the second part 1b. As an alternative, the two parts 1a, 1b could be otherwise assembled, for example, after having been manufactured in separate moulds. The whole external mould 10 with its cavity 11 filled with the artificial prostate 1 is cooled in a refrigerator.

As can be seen on FIG. 5, the result is a perfectly shaped artificial prostate 1, sensible to heat and with a density close to that of human prostate tissues, and containing heterogeneous 3D zones. In particular, the first part 1a comprises a closed outer surface surrounding the first artificial tissue and the second part 1b comprises a closed outer surface surrounding the second artificial tissue. The first 1a and second 1b parts are separate from each other and their outer surfaces do not fuse at locations where they contact each other. An interface mimicking a boundary between the peripheral zone and the transition zone is therefore formed at contacting locations of the outer surfaces of the first 1a and second 1b parts. Besides, the artificial lesion is placed within the first part 1a corresponding to the peripheral zone.

The artificial prostate 1 provides a contrast different from that of the artificial lesion on MRI images. Moreover, on FIGS. 6a and 6b which respectively show T2 weighted and Proton density weighted magnetic resonance images of the artificial prostate 1, the interface and, in the present case, the first part 1a and the second part 1b provide respective different contrasts on MRI images. The artificial lesion provides a contrast different from that of the artificial prostate 1 on ultrasound sonography images. Moreover, on FIG. 6c which shows a B-mode ultrasound image of the artificial prostate 1, the interface and, in the present case, the first part 1a and the second part 1b provide respective different contrasts on ultrasound sonography images.

Depending on the desired experimentation, the outer surface of the artificial prostate defines an internal volume between 30 cc and 80 cc, preferably between 40 cc and 50 cc.

Focal Therapy of a Prostate Cancer

A method for planning a focal therapy, and in particular a laser interstitial thermotherapy (LITT), of a prostate cancer will now be described as a non limitative example of an implementation of the above described prostate phantom.

To that end, provision is made of a system comprising, in addition to the prostate phantom:
  an interstitial thermotherapy laser comprising a laser source for emitting a light energy and at least one optical fibre connected to the laser source for guiding the light energy, a magnetic resonance imaging device as first imaging device for acquiring an image of the prostate phantom according to the first imaging modality, an ultrasound sonography device as second imaging device for acquiring an image of the prostate phantom according to the second imaging modality.

Generally speaking, the method comprises the step of treating the artificial lesion placed within the artificial prostate 1 arranged in the cavity 11 of the external mould 10 by placing the optical fibre within the prostate phantom and emitting the light energy by the laser source while imaging the prostate phantom with at least one of the magnetic resonance imaging device and ultrasound sonography device, and preferably with both devices by magnetic resonance imaging and transrectal ultrasound sonography.

Treatment and Evaluation of LITT

Material

The method has been performed using certified optical fibres of 600 µm in diameter avec optical diffuser of 10 mm (Pioneer Optics®; Reference: P/N 6021-00 Rev. 3; in accordance with recommendations of the Federal Drug Administration for CGMP, certified ISO 13485).

A laser diode emitting 980 nm radiations (Pharaon, OSYRIS France) has been used with a power of 5 W and a shot duration of 75 s in continuous mode for a fluence of 1145 J/cm².

As shown on FIGS. 7a, and 7b the gels of the artificial prostate are chosen to be sensitive to the thermal effect of the laser of the focal therapy system. The MR images of FIGS. 7a and 7b illustrate respectively a trajectory of the optical fiber of the focal therapy system, and the thermal effect around the tip of the fiber.

Evaluation of the Treatment

The evaluation of treatment using LITT on the artificial prostate 1 aimed to make sure that the different parts can be individualised in MRI imaging and that laser treatment can be quantified.

This phase has been conducted with a research dedicated MRI (Unit Biospec Brucker 7 Tesla). Various T1 and T2 weighting MRI sequences have been evaluated to obtain an appropriate signal making it possible to visualise the phantom and the treatment.

The volume of the lesions induced by LITT (according to selected parameters) has been an important data for treatment. Ten procedures have been performed on different artificial tissues with the same concentrations of the different components to calculate this volume. Considering that a necrosis zone induced by LITT corresponds to an ellipsoid with three axes, the volume of this necrosis zone has been obtained using the following formula:

$$V = 4/3 \times \pi \times A \times B^2$$

wherein A is half the length of the major axis of the treated zone (this axis corresponds to the path of the diffusing fibre), and B is half the length of the minor axis of the treated zone (this axis is perpendicular to the previous one), at a half-distance between distal and proximal ends of the zone.

The limits of the treatment zone have been identified as equivalent to MRI signal differences corresponding to the passage from the solid state to the liquid state of the material of the parts.

Bordering of necrosis zones induced by LITT and 3D reconstructions have performed by the software Osyrix® (version 3.5.1).

Planification of the Treatment

Dosimetric and conformational planification of the targeted zone during LITT treatment is an essential point, especially if the size of the lesion implies the use of several fibres. One of the efficient methods for such planification is simulation. During experimentation on animal model, thermal and optical simulation parameters of the thermal distribution and the cell damages resulting from LITT treatment have been validated on pre-clinical model with the software COMSOL Multyphysics (version 4.0).

For the implementation of this software to R3327-AT cell tumour tissue of the animal model, the known absorption and diffusion coefficients specific to that kind of tissue were used (Arnfield, 1992; Arnfield, 1988; Cheong, 1990). The path of the fibre within the tumour has been identified to determine an axis for dosimetric simulation. The simulation results have been compared to the volume of the necrosis actually obtained on the animal model using MRI after 48 hours. A very good correlation has been observed.

The application of the simulation on the phantom requires the knowledge of the optical properties and of the thermal conductivity of the human prostatic tissues. However the in vivo estimation of the latter was a difficult task. For this reason, it has been processed a different way. Actually, with the knowledge of the volume of the necrosis induced on the phantom by the LITT treatment with well defined parameters, several simulations were performed while varying the parameters used for the R3327-AT cells so as to converge towards the real volume. The parameters thus evaluated have been subsequently validated through repeated tests on the phantom with a modification of the laser shot parameters, among which the duration of the shot.

Treatment of the Prostate Phantom

This final phase aimed at obtaining results of a procedure similar to that which would be performed in a clinical protocol. Lindner et al. have disclosed this procedure for treating twelve patients selected during a clinical trial (Lindner, 2009). The same procedure has been performed except in the treatment control in real time by MRI rather than contrast sonography.

A sole diffusing fibre has been used for the treatment of the intraprostatic lesion. It has been positioned under sonographic control by transperineal route at the middle of the lesion (Toshiba Applio XG SSA-790A). It has been inserted using an introduction guide (Introduction Catheter Medlight iCAT-2.0-200 modified), under sonographic control, by means of a brachytherapy grid facing the artificial prostate. The treatment was performed under MRI control (Philips intera-achieva 1.5 T), with a protocol similar to that of a prostatic MRI performed in clinical practice (sequences TSE T2, BTFE, BFFE, echo of gradient T1 with angles at 3°, 10° and 17°). Two distinct containers containing oil and water have been disposed at the vicinity of the prostate phantom to calibrate the signal during the acquisitions.

The vascular nervous bands and the musculus sphincter have been modeled by thermocouples (Newport Omega). These have been connected to a system of acquisition (Omega Data Acquisition OMB-DAQ-55) and used to monitor the temperature in real time.

MRI observation makes visible the live effect of thermal laser shots in both gels.

Thanks to the two-part conception of the external mould, each procedure could be evaluated at a macroscopic scale through an incision of the artificial prostate along the axis of the fibre and a measurement of the treated zone.

Results

The dimensions and the global shape of the prostate and its surroundings are accurately reproduced.

The external mould 10 makes it possible to introduce, rotate and translate the endorectale ultrasonic probe to acquire ultrasound sonography images of the whole artificial prostate 1. The arrangement of an orthonormalised grid of brachytherapy in contact with the external mould 10 allows a positioning for accurate introduction of the LITT fibres.

The resiliency of the material of the external mould 10 mimics the properties of the human perineal tissue. The external mould 10 allows introduction of insertion catheters and then of LITT fibres through perineal and endorectal routes.

The whole prostate phantom is MRI compatible.

The effects of the treatment by laser thermotherapy have been evaluated by MRI 7T. The following parameters have been chosen:

sequences prior to laser treatment: T1 and T2 weighting spin-echo with TR of 800 ms and 6000 ms and TE of 11 ms et 60 ms respectively and a voxel size of 0.234 mm×0.234 mm×2 mm, sequences during laser treatment: T1 FLASH sequences with a voxel of 0.547 mm×0.547 mm×0.5 mm, the acquiring duration has been of 152 seconds.

The spatial resolution and the limited acquisition duration have been parameters considered for choosing the MRI sequences.

The mean volume of the treatment zone was of 1.21 cm$^3$ [1.12-1.31].

The thermal effect of the laser of the focal therapy system on the phantom are shown of FIGS. 8a and 8b. The induced lesion is shown.

The parameters corresponding to the volume of thermal damages of 1.2009 cm$^3$ were the following:

|  | Parameters | Values |
| --- | --- | --- |
| Thermal coefficients | k (W · mm$^{-1}$ · K$^{-1}$) | 5.52 * 10$^{-3}$ |
|  | ρ (g · mm$^{-3}$) | 0.950 * 10$^{-3}$ |
|  | C (J · g$^{-1}$ · K$^{-1}$) | 4.20 | wherein ρ (g·mm$^{-3}$) is the density, C (J·g$^{-1}$·K$^{-1}$) is the specific heat and k (W·mm$^{-1}$·K$^{-1}$) is the thermal conductivity.

Reproducible results (about 1 cm$^3$) are obtained after 10 laser shots with a diffuser fiber of 10 mm and a total light fluence of 1145 j/cm$^2$. These results are correlated to those obtained on preclinical model (Colin et al, BJU 2012) and those obtained using computer simulation (Marqa et al. BEO 2011).

The prostate phantom is visible in the different imaging modalities: endorectal ultrasound sonography and 1.5T MRI.

It has been possible to fully perform the LITT procedures according to the established protocol. Each diffusing fibre has been introduced through the brachytherapy grid in the prostate phantom. This introduction by perineal route has been made under control by endorectal sonography with placement of the fibre within the lesion. A sufficient contrast existed to distinguish the different structures of the phantom. The diffusing fibre was also visible.

In MRI, different structures are also identifiable. In T2 weighting, the artificial prostate appears in hypersignal and urethra in hyposignal. A low hyposignal shows the artificial lesion, deprived of gadolinium. The material used for endorectal sonography makes it possible to distinguish the rectum walls. In T1 weighting, the signal contrast is sharpened, making it possible to distinguish the different elements: urethra in hyposignal, lesion (without gadolinium) in hyposignal, and the remaining of the prostate in hypersignal. The introduction of the fibre is also visible in hypersignal.

The invention claimed is:

1. Prostate phantom for planning a focal therapy of a prostate cancer, said prostate phantom comprising an artificial prostate having an outer surface shaped to conform to a real prostate, and an artificial lesion arranged within the artificial prostate, said artificial prostate providing for a contrast different from that of the artificial lesion on an image acquired according to a first imaging modality, and said artificial lesion providing for a contrast different from that of the artificial prostate on an image acquired according to a second imaging modality, said second imaging modality being different from the first imaging modality, wherein the artificial prostate comprises:
a first part mimicking a peripheral zone of a zonal anatomy of the prostate, the first part being made of a first artificial tissue and comprising a closed outer surface,
at least a second part separate from the first part and mimicking at least a second zone of the zonal anatomy of the prostate, the second part being made of a second artificial tissue and comprising a closed outer surface,
the first and second parts contacting each other along an interface mimicking a boundary between the peripheral zone and the second zone.

2. Prostate phantom according to claim 1, wherein the first artificial tissue and the second artificial tissue are different from each other to provide respective different contrasts on an image acquired according to the first imaging modality and on an image acquired according to the second imaging modality.

3. Prostate phantom according to claim 2, wherein each of the first and second artificial tissues comprises:
a ballistic gel made of gelatin between 1% w/w and 10% w/w and water between 90% w/w and 99% w/w
a first contrast agent visible on the image acquired according to the first imaging modality, a concentration of the first contrast agent for the first artificial tissue being different from a concentration of the first contrast agent for the second artificial tissue.

4. Prostate phantom according to claim 3, wherein the first contrast agent comprises gadolinium visible on the image acquired by magnetic resonance imaging.

5. The prostate phantom of claim 3, wherein at least one of said first and second artificial tissues comprises a ballistic gel comprising 4% w/w gelatin.

6. The prostate phantom of claim 3, wherein at least one of said first and second artificial tissues comprises a ballistic gel comprising 96% w/w water.

7. Prostate phantom according to claim 1, wherein the first part is moulded over the second part.

8. Prostate phantom according to claim 1, wherein the artificial lesion is made of a third artificial tissue comprising:
a ballistic gel made of gelatin between 1% w/w and 10% w/w and water between 90% w/w and 99% w/w
a second contrast agent visible on the image acquired according to the second imaging modality.

9. Prostate phantom according to claim 8, wherein the second contrast agent comprises haemoglobin visible on the image acquired by ultrasound sonography.

10. The prostate phantom of claim 8, wherein said third artificial tissue comprises a ballistic gel comprising 4% w/w gelatin.

11. The prostate phantom of claim 8, wherein said third artificial tissue comprises a ballistic gel comprising 96% w/w water.

12. Prostate phantom according to claim 1, wherein the artificial lesion is placed within the first artificial tissue.

13. Prostate phantom according to claim 1, wherein the outer surface of the artificial prostate defines an internal volume between 30 cc and 80 cc.

14. The prostate phantom of claim 13, wherein said internal volume is between 40 cc and 50 cc.

15. Prostate phantom according to claim 1, further comprising an external mould having an outer surface and including internally a cavity for accommodating the artificial prostate, the external mould comprising:
- a first conduit having a wall arranged close to the cavity, and an end opening in the outer surface, said first conduit mimicking a rectum with an anal orifice,
- a second conduit having a wall and two ends opening in the outer surface and in the cavity, respectively, said second conduit mimicking an urethra,
- at least the walls of the first and second conduits being made of a material mimicking a perineal tissue.

* * * * *